(12) United States Patent
Redey et al.

(10) Patent No.: US 7,632,384 B1
(45) Date of Patent: Dec. 15, 2009

(54) MULTI-FUNCTIONAL SENSOR SYSTEM FOR MOLTEN SALT TECHNOLOGIES

(75) Inventors: Laszlo Redey, Downers Grove, IL (US); Karthick Gourishankar, Downers Grove, IL (US); Mark A. Williamson, Naperville, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 738 days.

(21) Appl. No.: 11/288,057

(22) Filed: Nov. 18, 2005

Related U.S. Application Data

(60) Provisional application No. 60/692,239, filed on Jun. 21, 2005.

(51) Int. Cl.
*G01N 27/26* (2006.01)
*G01F 1/64* (2006.01)

(52) U.S. Cl. .................. 204/422; 204/408; 204/419; 205/783.5; 205/786; 205/790; 205/793; 205/794.5

(58) Field of Classification Search ......... 204/400–435; 205/775–794.5
See application file for complete search history.

(56) References Cited

U.S. PATENT DOCUMENTS

| | | | | |
|---|---|---|---|---|
| 4,414,093 | A * | 11/1983 | Redey et al. ................. | 204/412 |
| 4,601,810 | A * | 7/1986 | Tiwari et al. ................. | 204/413 |
| 5,632,881 | A * | 5/1997 | Gabelich et al. ......... | 205/781.5 |
| 6,514,394 | B1 * | 2/2003 | Vangrunderbeek et al. .. | 204/400 |
| 6,540,902 | B1 * | 4/2003 | Redey et al. ................. | 205/354 |

* cited by examiner

*Primary Examiner*—Brian J Sines
*Assistant Examiner*—Christopher R Graham
(74) *Attorney, Agent, or Firm*—Mark C. Lang; Brian J. Lally; Paul A. Gottlieb

(57) ABSTRACT

The present invention relates to a multi-functional sensor system that simultaneously measures cathode and anode electrode potentials, dissolved ion (i.e. oxide) concentration, and temperatures in an electrochemical cell. One embodiment of the invented system generally comprises: a reference(saturated) electrode, a reference(sensing) electrode, and a data acquisition system. Thermocouples are built into the two reference electrodes to provide important temperature information.

20 Claims, 7 Drawing Sheets

MULTI-FUNCTIONAL SENSOR SYSTEM FOR MOLTEN SALT TECHNOLOGIES

RELATION TO OTHER APPLICATIONS

The present non-provisional application claims priority to U.S. Provisional Patent Application No. 60/692,239 filed on Jun. 21, 2005 by instant inventors, which is hereby incorporated by reference in its entirety.

CONTRACTUAL ORIGIN OF THE INVENTION

The United States Government has rights in this invention pursuant to an Agreement between the U.S. Department of Energy and The University of Chicago, DOE Contract No. W-31-109-ENG-38.

FIELD OF INVENTION

The present invention relates to a multi-functional sensor system for electrochemical cells in general and molten-salt cells in particular. The invented system simultaneously measures cathode and anode electrode potentials, dissolved ion (i.e oxide) concentration, and temperature in electrochemical cells.

BACKGROUND OF THE INVENTION

The present invention refers to a multi-functional sensor system for electrochemical cells, especially those related to molten salt technologies. Accurate and reliable dissolved ion concentration and potential measurements are crucial to cell control, operation, and optimization. However, the accuracy of concentration measurements rely on accurate temperature measurements at each sensor location. State of the art sensor systems do not provide adequate temperature measurements, and thus they do not provide accurate dissolved oxide concentrations.

With a reliable knowledge of temperature, concentration, and potential variations in the cell, the cell can be mapped out to provide a model that can be used both as a diagnostic and an optimization tool.

Molten salt systems present additional challenges due to the corrosive nature of the electrolyte and the high operating temperatures of the cell. Thus another challenge is to find chemically compatible reference electrode materials for use in molten salt environments There is a need for a multi-functional sensor system that simultaneously measures cathode and anode potentials, dissolved oxide concentration, and temperatures in electrochemical cells, to provide accurate, temperature dependent readings.

SUMMARY OF THE INVENTION

The present invention relates to a multi-functional sensor system that simultaneously measures cathode and anode electrode potentials, dissolved ion (i.e. oxide) concentration, and temperatures in the electrochemical cell. One embodiment of the invented system generally comprises: two reference electrodes an R(saturated) electrode and an R(sensing) electrode, and a data acquisition system. Thermocouples are built into the two R electrodes to provide important temperature information.

The present invention has a multitude of applications including: molten-salt based pyroprocessing applications such as recovery of actinides from spent nuclear fuels, direct electrochemical reduction (sometimes referred to as electrolytic reduction), electrowinning, electrorefining, chemical reduction (reductive extraction), and dissolution. The invented system can also be employed in: metals extraction and alloy fabrication processes such as extraction of titanium and other important metals and alloys using molten-salt processing schemes, batteries and solid-oxide fuel cell technologies, the iron, steel and aluminum industries.

While some of the applications such as pyroprocessing and titanium metal extraction may use the electrolyte systems described herein, other applications may be adapted for use with different electrolyte systems. The invention could be used as a process monitoring and process control device for many industrial processes in the, primary metal extractions, chemical and nuclear industries. For background information on reference electrodes for molten systems see, "Molten Salt Techniques", Chapter 4, Vol. 3, 1987, Plenum Press, which is herein incorporated by reference in its entirety.

BRIEF DESCRIPTION OF THE DRAWINGS

For the purpose of facilitating an understanding of the invention, there is illustrated in the accompanying drawings and graphs.

DETAILED DESCRIPTION OF THE INVENTION

Figure 1:
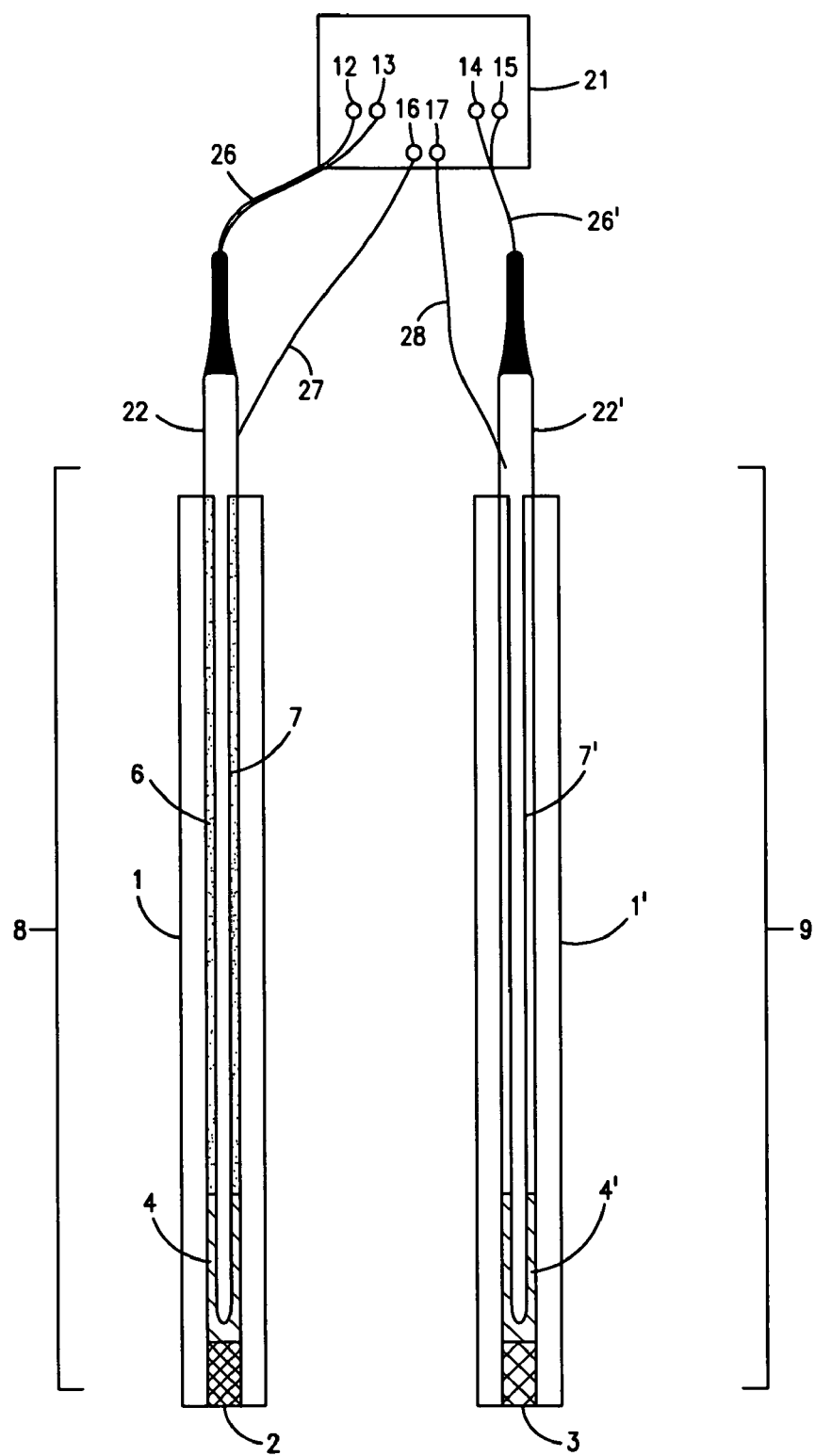
FIG. 1 is a schematic illustration of one embodiment of the invention comprising a R(saturated) electrode, a R(sensing) electrode and a data acquisition system.

One preferred embodiment of the invented system generally comprises: a R(saturated) electrode, a R(sensing) electrode and a data acquisition system as shown in FIG. 1. This system is based on a Ni/NiO/LiCl/$Li_2O$ system, where the electrode potential response depends on the concentration of dissolved lithium oxide.

The exemplary sensor system illustrated in FIG. 1 generally comprises: a saturated electrode R(saturated) 8, a sensing electrode R(sensing) 9, and a data acquisition system 21 to which both electrodes are connected. The outer parts of the two R electrodes 8 and 9 have a vary similar construction, except that their diffusion barriers 2 and 3 are different.

The reference electrodes generally comprise: an outer tube 1 (1'), a diffusion barrier 2 or 3, a first oxide (i.e. NiO) 4 (or 4') and thermocouple 7 (or 7'). The R(saturated) electrode 8 also contains a second oxide (i.e. $Li_2O$ or CaO) 6. The outer tube 1 is preferably electrochemically inactive.

The outer tube 1 (or 1') of the electrodes 8 and 9 are made out of high density MgO: However, the tube 1 can be made of a variety of high-density materials that can withstand the conditions of the cell being tested. Suitable materials include but are not limited to high density ceramics like MgO, $Al_2O_3$. and combinations thereof. The physical dimensions of the outer tube 1 will vary according to desired use, results, components, and a host of other factors.

R(Saturated) Electrode

The outer tube 1 of the R(saturated) electrode has a top portion, a middle portion, and a lower portion.

Figure 4:
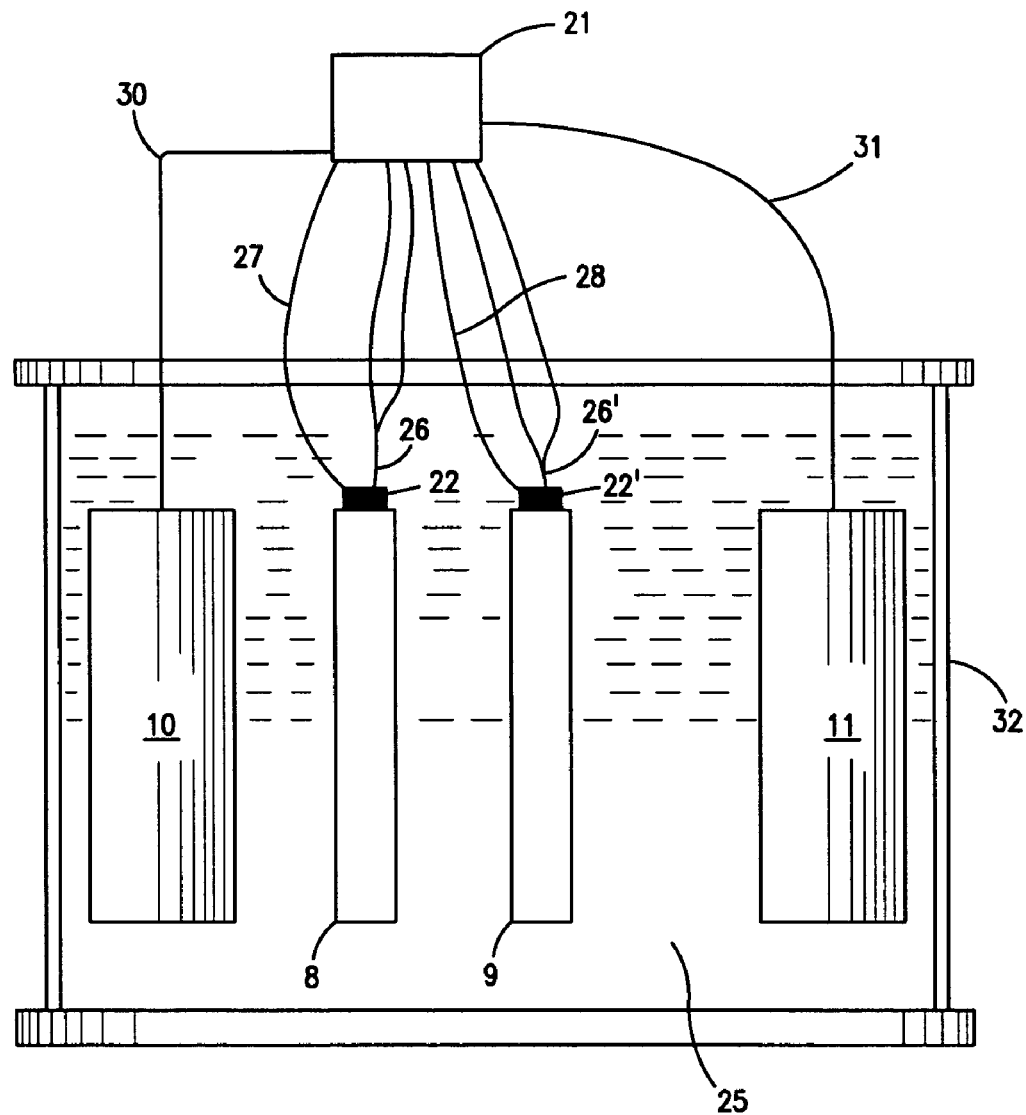
FIG. 4 illustrates how the invention might be used in an electrochemical cell system.
Figure 9:
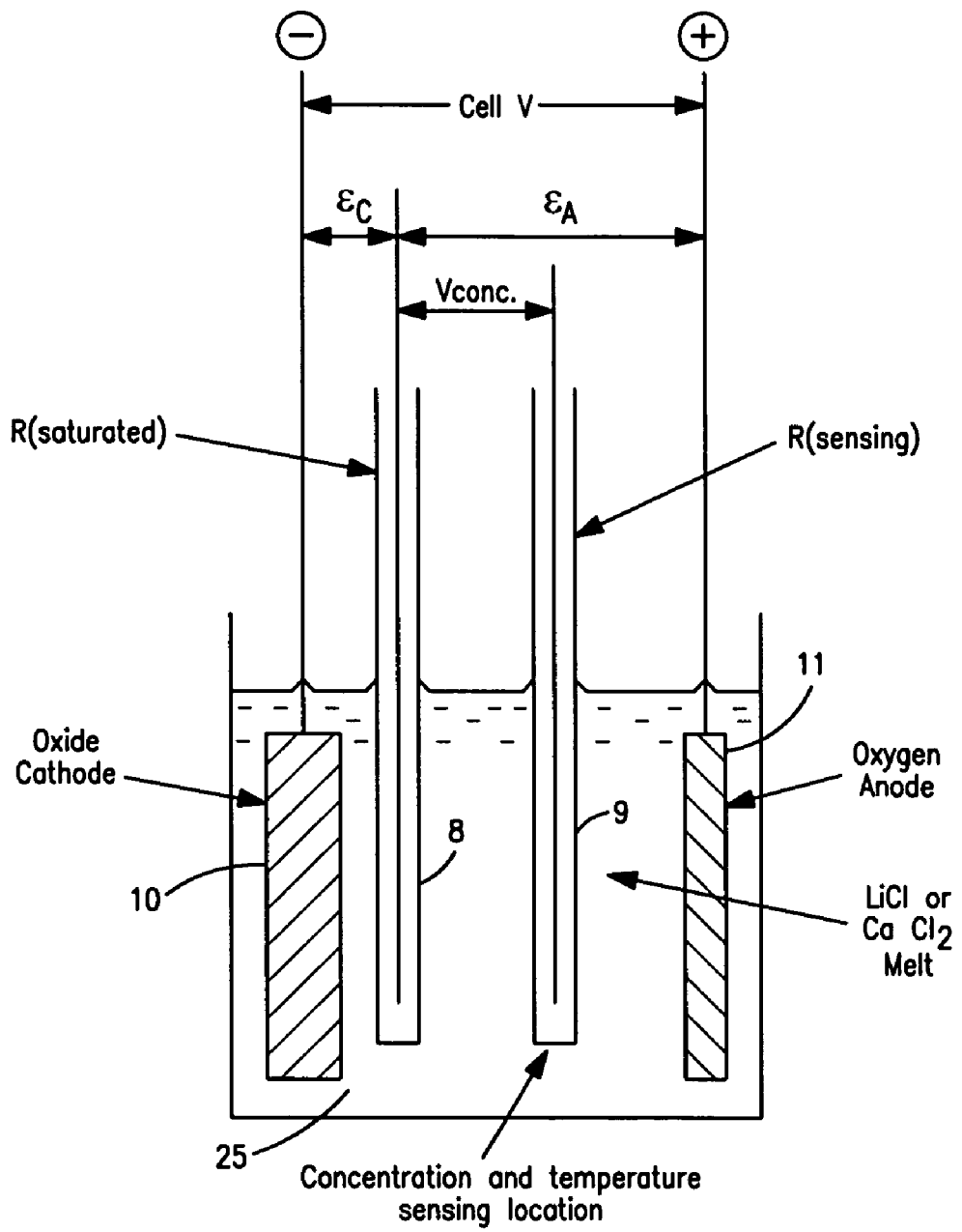
FIG. 9 is an example of the multi-functional sensor used in conjunction with a working or test electrochemical cell.

The lower portion of the electrode 8 is filled (i.e. plugged) with a dense diffusion barrier 2. The diffusion barrier 2 for the R(saturated) electrode (ion communication with the bulk cell electrolyte 25 (See FIG. 4 or 9) should prevent or at least minimize leakage of $Li_2O$ (or equivalent) from the reference electrode 8 into the bulk electrolyte 25 (FIG. 4 or 9). Various high density materials can be used as the barrier 2 including but not limited to high density ceramics like MgO, $Al_2O_3$, and combination thereof. Alternatively, a less dense (but longer) plug could be used, giving a similar effect of creating a barrier with low diffusion rate of $Li_2O$.

It is important to note that while the porous barrier 2 should act as a diffusion barrier it cannot be an insulating barrier. The resistance of the barrier 2 in R(saturated) should be preferably less than about 1 MΩ. A suitable ceramic barrier 2 is a high-density MgO plug manufactured by Ozark Technical Ceramics, Inc. (Webb City, Mo.).

A coaxial, thermocouple 7 having a lower thermosensing end and an upper communication end is inserted into the outer tube 1.

Figure 2:
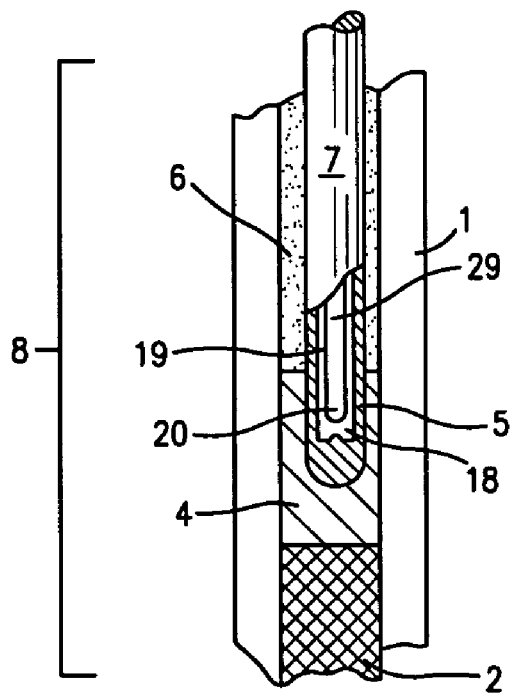
FIG. 2 is a partial cut-away view of an exemplary R(saturated) electrode.

The thermocouple 7 comprises a thermosensing device 29 surrounded by a nickel sheathing 5. See FIG. 2. The thermocouple 7 is inserted so that its lower thermosensing end 19 is positioned near the lower portion of the outer tube 1, just above the diffusion barrier 2, as shown in FIG. 2.

The lowest part of the thermosensing end 19 houses the bi-metallic portion of the thermosensing device 20. An insulator (i.e. MgO) 18 resides between the thermosensing material 29 and the nickel sheathing 5 of the thermocouple 7. The thermocouple 7. The thermocouple can be held in position in a number of ways known in the prior art. For example, an adaptor (not shown) can be used to engage the upper end of the thermocouple using a screw type attachment device as is known in the art, See, U.S. Pat. No. 4,414,093, issued to Redey et al., which shows an example and is hereby incorporated by reference in its entirety. Other ways of holding the thermocouple in place are well known in the art.

The upper end of the thermocouple 7, includes a thermocouple head 22 that extends out the outer tube 1, and an electrical lead 26 that extends outward from the thermocouple head 22 to provide communication with a data acquisition system for converting voltage measurements by the bi-metallic portion 20 of the thermosensor into a temperature reading. See FIG. 1.

The thermocouple 7 is sheathed in nickel 5 and acts as part of the Ni/NiO reference electrode and a voltage lead. The thermocouple head 22 (also nickel sheathed) acts as a good voltage lead. (FIG. 2.)

While a variety of ungrounded thermocouples can be used the thermocouple 7 is preferably an ungrounded, k-type thermosensor, with nickel sheathing. As noted the nickel sheath 5 makes the thermocouple double as a Ni/NiO reference electrode and voltage lead.

One suitable thermocouple is a k-type thermocouple manufactured by Omega Engineering, Inc. (Stamford, Conn.). Non-sheathed electrodes could be utilized if they are placed in a tube of the metal of choice (i.e. Ni). See, U.S. Pat. No. 4,414,093 issued to Redey et al., which is hereby incorporated by reference in its entirety. Although, ungrounded thermocouples are preferred for use in both electrodes, grounded electrodes could be employed in certain arrangements.

A first metal oxide (phase) 4 is filled around the lower end of the coaxial thermocouple 7, as shown in FIG. 1. There must be enough NiO to ensure that at least part of the Ni sheath of the thermocouple 5 is always in contact with NiO. The amount of NiO necessary depends on the "leak rate" which is dependent upon properties of the porous barrier 2 and the desired service life of the electrode. As is discussed later, NiO can be replaced by another oxide or other phases (i.e. fluorides, bromides etc.) when a different electrode/electrlolyte system is being used.

Alternatively a thin layer of NiO (or other desired phase) can be electrochemically formed on the surface of the nickel sheathing of the thermocouple 7'

The R(saturated) electrode 8 includes a second metal oxide 6. In the illustrated embodiment the second metal oxide is $Li_2O$. The amount of $Li_2O$ (or CaO) in R(saturated) depends on the size of the electrode, the anticipated "leak" rate of $Li_2O$ and the desired service life of the device. The second metal oxide 6 is positioned around the coaxial thermocouple 7 and layered on top of the first metal oxide 4, as shown in FIGS. 1 and 2. While a layered configuration is shown in the figures, the first and second oxides (phases) can be mixed together.

The amount of $Li_2O$ (or CaO) must be sufficient to saturate the bulk electrolyte 25 (i.e. LiCl or $CaCl_2$ inside R(saturated) with $Li_2O$ (or CaO) during cell operation. For example, the solubility limit of $Li_2O$ in LiCl at 650° C. is 11.9 mol. % (8.7 wt. %). So enough $Li_2O$ must be contained within R(saturated) to at least saturate (excess is desirable) whatever volume of LiCl is contained within the R(saturated). In practice it is preferable to have a large excess of $Li_2O$ in R(saturated).

The R(saturated) electrode's 8 substantial amount of a solid lithium oxide (or calcium oxide) keeps the melt inside at saturation, thus providing a thermodynamically defined standard reference electrode system for measuring electrode potentials and a concentration reference for concentration measurement. As is discussed later, $Li_2O$ can be replaced by other materials in other electrode/electrlolyte systems.

R(Sensing) Electrode

The R(sensing) electrode 9 also has an outer tube 1' with a top portion, a middle portion, and a lower portion. As noted earlier the R(sensing) 9 electrode is constructed similarly to that of the saturated electrode 8.

One of the differences between the electrodes is that the lower portion of the R(sensing) electrode 9 consists of a different type of diffusion barrier 3. The R(sensing) electrode 9 requires a highly porous (diffusion) barrier 3 that allows the sensing electrode to respond rapidly to changes in cell bulk electrolyte concentration at the particular location. In other words the diffusion barrier 3 in the R(sensing) electrode should allow for rapid equilibration of the concentrations inside and outside the reference electrode to decrease response time.

In general diffusion barriers for the sensing electrode 9 can be made by a variety of other methods. For example drilling a small hole in a closed-end tube or intentionally introducing a crack in a closed-end tube could also provide a diffusion barrier and serve the same purpose as a porous plug. A diffusion plug 3, for the sensing electrode is low density MgO plug manufactured by Ozark Technical Ceramics, Inc. (Webb City, Mo.).

Figure 3:
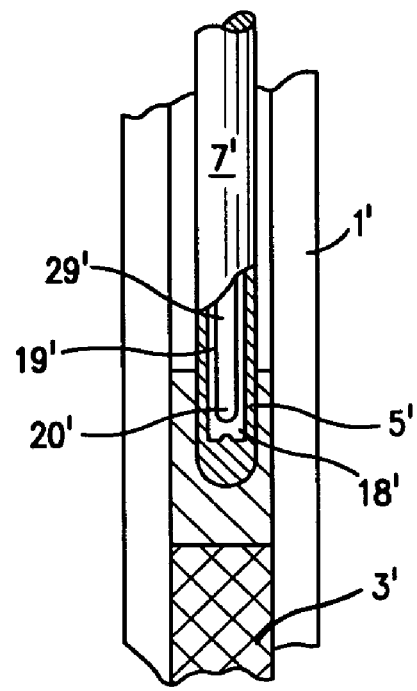
FIG. 3 is a partial cut-away view of an exemplary R(sensing) electrode.

Similar to the R(saturated electrode) 8, a coaxial, thermocouple 7' having a lower thermosensing end and an upper communication end is inserted into the outer tube 1 of the R(sensing) electrode 9. The thermocouple 7' is inserted so that its lower thermosensing end 20' is positioned near the lower portion of the outer tube 1', just above the diffusion barrier 2, as shown in FIG. 3. The upper end of the thermocouple 7', includes a thermocouple head 22' that extends out the outer tube 1', and an electrical lead 26' that extends outward from the thermocouple head 22'. The thermocouple 7' is similar to the one described earlier.

An adapter (not shown) can be used to screwingly (or otherwise) engage the upper end of the thermocouple with the upper portion of the outer tube as is known in the art. An example of this is illustrated in U.S. Pat. No. 4,414,093 issued to Redey et al. The other characteristics of the thermocouple 7' are similar to the thermocouple of the R(saturated) electrode. Other adapter means for holding the thermcouples in place can be imagined.

Like R(saturated) a first metal oxide (i.e. NiO) 4' is filled around the lower end of the coaxial thermocouple 7', as shown in FIGS. 1 and 3. There must be enough NiO to ensure that at least part of the Ni sheath 5' of the thermocouple is always in contact with NiO. Alternatively a thin layer of NiO (or other desired phase) can be electrochemically formed on the surface of the nickel sheathing of the thermocouple 7'. As is discussed later, NiO is the preferred first metal oxide but can be replaced by other phases.

Data Acquisition System

The two reference electrodes 8 and 9 are attached to a central data acquisition system 21. The acquisition system 21 should be a multi-channel data system capable of taking several types of measurements including: thermocouple readings and potential measurements. The electrodes 8 and 9 are connected to the data system 21 via a series of connecting wires.

More specifically, electric lead 26 of the R(saturated) electrode is connected to first and second thermocouple terminals 12 and 13 of the data acquisition system (can be a compatible connecting wire).

The head of the nickel sheathed electrode 22 is connected to the first electrode terminal 16 of the data acquisition system 21 via a connecting wire 27.

Similarly the electric lead of the thermocouple 26' of the R(sensing) electrode is connected to the third and fourth thermocouple terminals 14 and 15 of the data acquisition system 21 (can be via a connecting wire.)

The head of the nickel sheathed electrode 22' is connected to the second electrode terminal 17 of the data acquisition system via a connecting wire 28.

A suitable data acquisition system is manufactured by HP-Agilent.

Preferred Reference Electrode Materials

Ni/NiO is the preferred electrode material because it satisfies three major requirements for a stable and reliable reference electrode namely that: (1) it does not react with the preferred electrolytes (LiCl/Li$_2$O or CaCl$_2$/CaO) and is thus relatively inert to the chemical environment; (2) it has very low solubility, if any, in the electrolyte; and (3) nickel is known to exist in only one stable oxidation state (2+) and this in turn allows for a stable reference thermodynamic potential (that corresponding to Ni/Ni$2^+$ equilibrium) to be established over a wide practical range of process/cell conditions. In addition, both Ni and NiO are solids at the operating temperatures of molten salt cells (610° C.-1000° C.) making them easy to contain. Solids also allow one to easily maintain good contact between the two phases (Ni and NiO) in the construction of the reference electrodes.

Alternate Electrode Materials

It should be noted that there are potential alternatives to Ni/NiO for use in LiCl—Li$_2$O and CaCl$_2$—CaO electrolyte systems although so far none have been shown to work as well as the Ni/NiO reference electrode. For example Fe/Fe$_3$O$_4$ or Fe/Fe$_2$O$_3$ are potential alternatives. But the multiple oxidation states of iron (+2, +3) would limit the stability range of this reference electrode system. Other alternatives can be used in non-molten cells, as is well known in the art.

For example, Li/Li$_2$O and Ca/CaO reference electrodes may prove useful, especially if it is desirable to have materials (in the reference electrode construction) that are similar to those present in the electrolyte system. However, because Li and Li$_2$O are significantly soluble in LiCl (as are Ca and CaO in CaCl$_2$) they limit the service life of the reference electrode. In addition Li and Ca are liquids at the operating temperatures and thus pose an extra hurdle in the fabrication of the reference electrode.

Alternate Electrolyte Systems

CaCl$_2$—CaO electrolyte systems may prove preferable to LiCl—Li$_2$O in cells where a more powerful reducing potential is desired. For example reduction of highly stable rare-earth-oxides such as Nd$_2$O$_3$ and La$_2$O$_3$ to their respective metallic states would require a CaCl$_2$ electrolyte system rather than a LiCl electrolyte system. CaCl$_2$ is also preferable to LiCl when the desirable process operating temperature is higher. Typically LiCl-cells operate at around 650° C. while CaCl$_2$-cells operate at around 850° C.

Other electrolyte systems, may also be employed. For example, some oxides have higher solubilities in molten fluoride electrolytes and thus molten fluoride systems will be of interest in applications where the goal is to dissolve these oxides in the electrolyte and then recover them by an electrowinning process. In our patented electrochemical reduction process ("Direct Electrochemical Reduction of Metal-Oxides", L. Redey and K. Gourishankar, U.S. Pat. No. 6,540,902, Apr. 1, 2003, which is hereby incorporated by reference in its entirety) oxides are directly converted to metals at the cathode and these oxides of interest do not dissolve in the electrolyte.

Ni/NiO or analogous systems to Ni/NiO can be potentially used in other molten salt systems. For example in molten fluorides Ni/NiO can probably be used for a similar purpose (i.e. measuring electrode potentials, dissolved oxide concentration as well as temperature). This is quite likely to be the case for other molten salt systems based on iodide salts, bromide salts, sulfide salts, chloride salts, etc. The key is to identify a couple (like Ni/NiO) with the right chemistry and physical properties given the cell operating conditions (electrolyte, temperature, etc.).

Just as the use of NiO phase allows for measuring dissolved oxide concentration in the electrolyte, the use of nickel-fluoride phases (or some other metal/metal-fluoride system) can in principle help track dissolved fluoride concentrations in cells where this is of interest. But it is important to ensure that the fluoride used in the reference electrode is virtually insoluble in the fluoride melt of interest.

In non-molten-salt technologies such as batteries and fuel cells, for example, again the Ni/NiO reference electrode or any other similar reference electrode system can be used in principle. However, each cell and electrolyte system must be carefully evaluated to ensure that the reference electrode is chemically and physically compatible and that it can be used for reliable and stable measurements over long periods of time.

In summary Ni/NiO is preferred, but not essential and it can be replaced with other materials and it will have to be replaced with other materials depending on the electrolyte system, cell operating condition, and the dissolved ion of interest. However what is crucial is that all the physical and chemical characteristics of the material must be compatible and it should be easy to fabricate a simple, compact device that is capable of simultaneously providing multiple signals relating to electrode potentials, concentration of interest, and temperature. In practice, the specific cell conditions and electrolyte systems may be such that it may severely limit the universe of materials available for the device construction.

Measuring Ion (i.e. Oxide) Concentration

To measure dissolved ion (i.e. oxide, flouride) concentrations, it is necessary to establish a reference (known) thermodynamic potential and this is accomplished by using $Li_2O$-saturated LiCl in R(saturated) or CaO-saturated $CaCl_2$ in R(saturated). If we used some other oxide material instead of $Li_2O$ or CaO we will not be able to track the dissolved $Li_2O$ or CaO concentration respectively in the electrolyte which is operationally and technologically very important to monitor and control. Again, if our interest is say dissolved LiF concentration in a fluoride-containing electrolyte, we would use something like a Ni/Ni-fluoride/LiF-containing-fluoride electrolyte (with a saturated or a known fixed concentration of LiF) kind of reference electrode construction to monitor the dissolved LiF concentration (provided that it satisfies all other physical, chemical, and fabrication requirements).

Dissolved $Li_2O$ concentration in the electrolyte is obtained from the voltage difference between R(saturated) and R(sensing). See FIG. 9. FIGS. 4 and 9 show the invented sensor system being used within a cell system. The saturated electrode 8, sensing electrode 9, and two working (cell) electrodes are placed in bulk electrolyte 25 within a working cell 32 and connected to a data acquisition system 21, via various connecting wires 26,26',27,28,30 and 31. We have measured the dissolved $Li_2O$ concentration in LiCl—$Li_2O$ melts using this arrangement.

Figure 7:
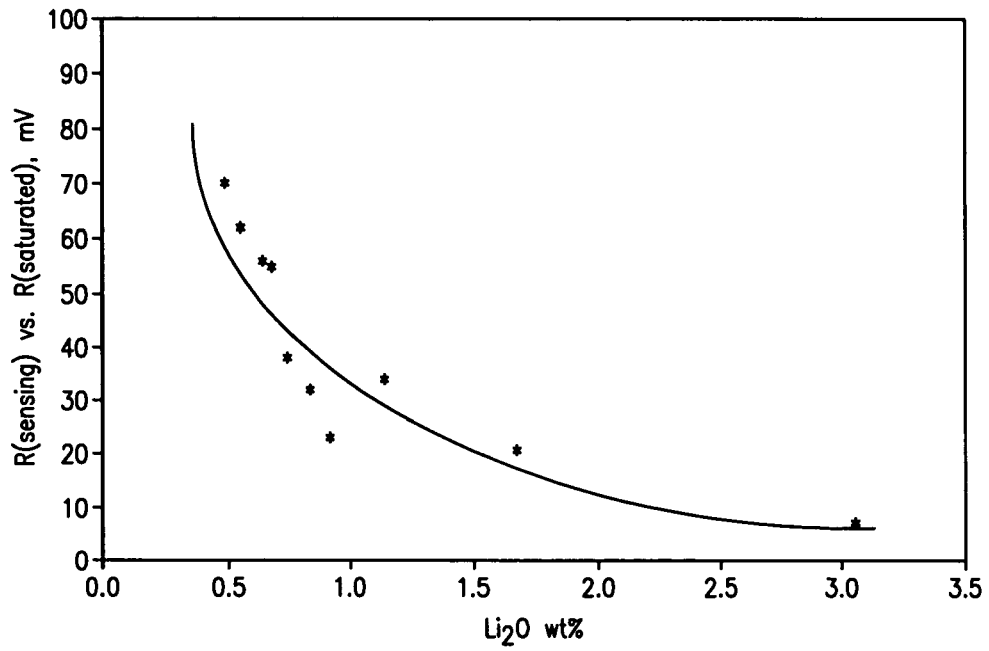
FIG. 7 is a calibration curve for measuring dissolved $Li_2O$ concentration in LiCl—$Li_2O$ melts at 650° C. using a combination of sensing and saturated Ni/NO reference electrodes.

An example is illustrated in the calibration curve shown in FIG. 7. Monitoring and control (optimization) of oxide concentration is very important in these molten-salt based technologies because of economic and safety reasons. For example, the dissolved oxide concentration will have to be maintained below a threshold value for the efficient and complete conversion of oxides like $Pu_2O_3$ and $Am_2O_3$ to their metallic forms in the reduction of oxide spent nuclear fuels. On the other hand if the oxide concentration is very low, the process will be slow and could lead to unwanted side reactions at the anode.

The dissolved oxide concentration measurement in LiCl is based primarily on the following relationship:

$\Delta\epsilon = RT/(nF) * \ln(a_{Li2O, sense}/a_{Li2O, saturating})$ $\Delta\epsilon$=EMF (potential) between R(sensing) and R(saturated)
$a_{Li2O, sense}$=activity of dissolved $Li_2O$ in the cell electrolyte
$a_{Li2O, saturated}$=1=activity of $Li_2O$ in R(saturated)
T=melt temperature (in K)
R=universal gas constant Thus the activity, $a_{Li2O\ sense}$, can be directly measured at R(sensing) location from the measured EMF. Now $a_{Li2O}$ is related to the concentration of $Li_2O$, $x_{Li2O}$ (given in mole fraction), by the following equation:

$$a_{Li2O} = Y_{Li2O} * x_{Li2O}$$

where $Y_{Li2O}$=activity coefficient of $Li_2O$ and is typically measured as a function of temperature for a given concentration range.

When measuring oxide concentration the potential of the second electrode R(sensing) 9 is compared to R(saturated) 8. The oxide concentration of the inner compartment of the R(sensing) electrode 9 follows that of the cell electrolyte due to diffusion. Diffusion is facilitated by a low resistance barrier 3, which also keeps out impurities. On the contrary, the barrier 2 in R(saturated) 8 is very dense to minimize outward-diffusion of the lithium (or calcium) oxide.

Measuring Potentials

The reference electrodes can be used for determining anode and cathode potentials. Providing voltage measurements between the reference electrode 8 or 9 and a working electrode 10 or 11, allows one the measure the electrode potential of the working electrode 10 or 11 which can be used to help measure, design, and operate optimal working electrodes for specific conditions. The thermocouples 7 and 7' allows one to calculate temperature dependent voltage measurements which is important.

Figure 5:
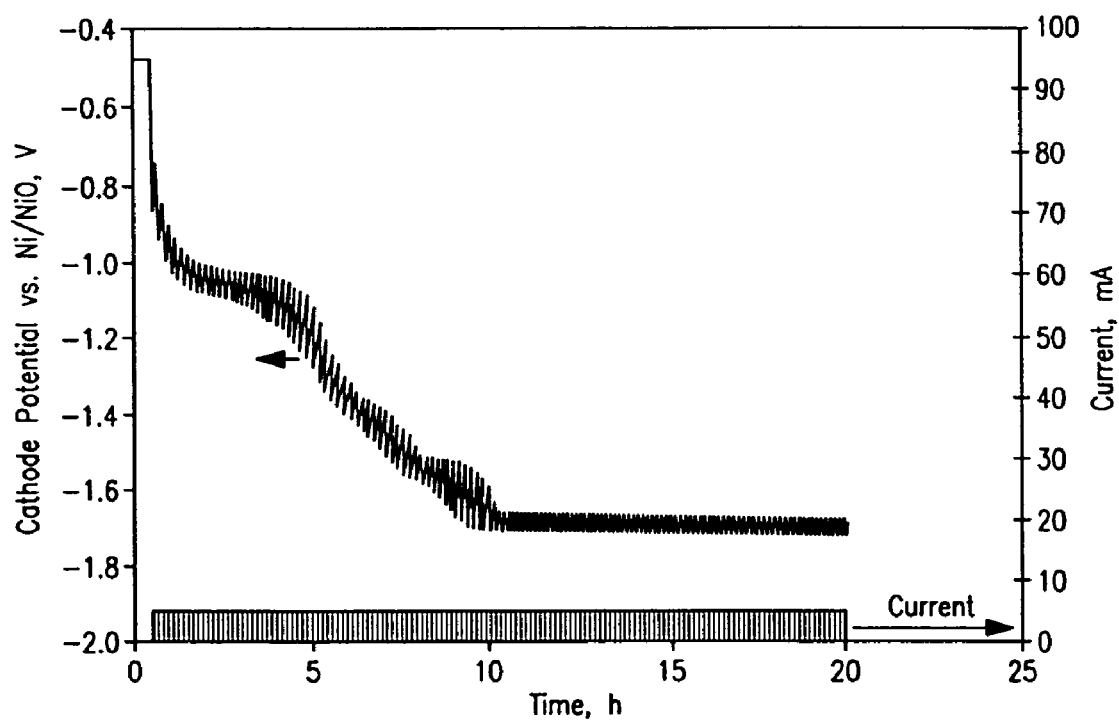
FIG. 5 is a graph of cathode potential measured vs. a Ni/NiO reference electrode in the electrochemical reduction of $UO_2$, a current-interrupted couolmetric titration experiment designed to study the mechanism of $UO_2$ direct electrochemical reduction in a LiCl-1 wt % $Li_2O$ melt at 650° C.
Figure 6:
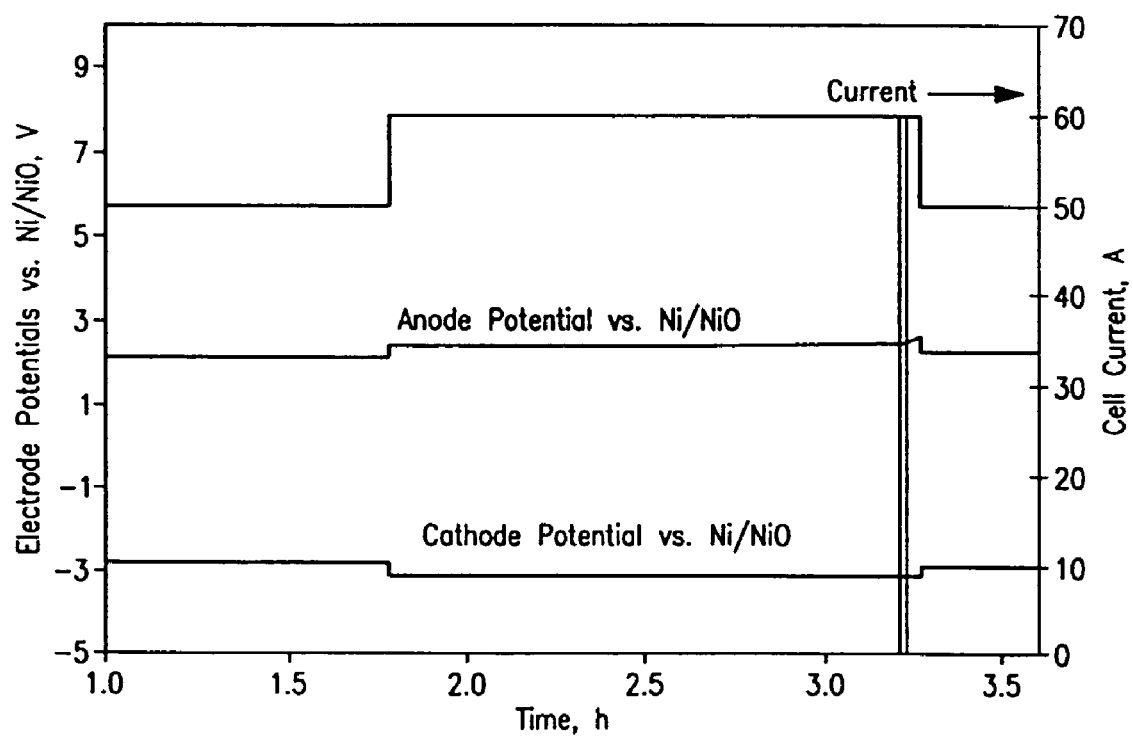
FIG. 6 is a graph of anode and cathode potentials measured vs. a Ni/NiO reference electrode in the direct reduction of a 1 kg-batch $UO_2$ charge in a LiCl-1 wt % $Li_2O$ melt at 650° C. In this cell the reference electrode was placed close to the anode and away from the cathode, thus a significant cathode polarization is observed.

The reference electrodes can also be used for determining anode and cathode potentials in a variety of experiments—in LiCl/$Li_2O$ cells, $CaCl_2$/CaO cells, etc. We have used, depending on the experiment, either R(saturated) or R(sense) for electrode potential measurements. Illustrative examples of applications in both fundamental measurements and production cells are shown in FIGS. 5 and 6. The graphs are examples of a potential scale constructed using the reference electrode as a zero point Temperature Effects Temperature can significantly effect potentials. First, there can be spatial variations in temperature within the cell. Assume that there are two sensing electrodes, $R_1$(sensing) and $R_2$ (sensing), at two locations in the cell where the local temperatures are $T_1$ and $T_2$ K respectively. The difference in the measured R(sensing) vs. R(saturated) potentials at the two sensing locations can then be expressed as:

$$\delta(\Delta\epsilon) = \Delta\epsilon_1 - \Delta\epsilon_2 = R/(nF) * (T_1 * \ln(a_{Li2O, sense\ 1}) - T_2 * \ln(a_{Li2O, sense\ 2}))$$

For example, a 10 K temperature difference could give rise to a 1 mv error in measuring a 1 mol. % $Li_2O$ concentration at two spatial sensor locations where the temperatures are 650 and 660° C. Another source of temperature error is when R(saturated) is at a different temperature from R(sensing). As the temperature difference becomes larger, depending on how the activity ($\alpha_{Li2O}$) activity coefficients ($gama_{Li2O}$) vary with temperature, the error can be rather large. There can be significant temperature variations between locations and even at a single location in an electrochemical cell given effects such as thermal convection, gas evolution etc. That is why for an accurate measurement is very important to know the precise temperature at all times and at each of the sensor location.

Figure 8:
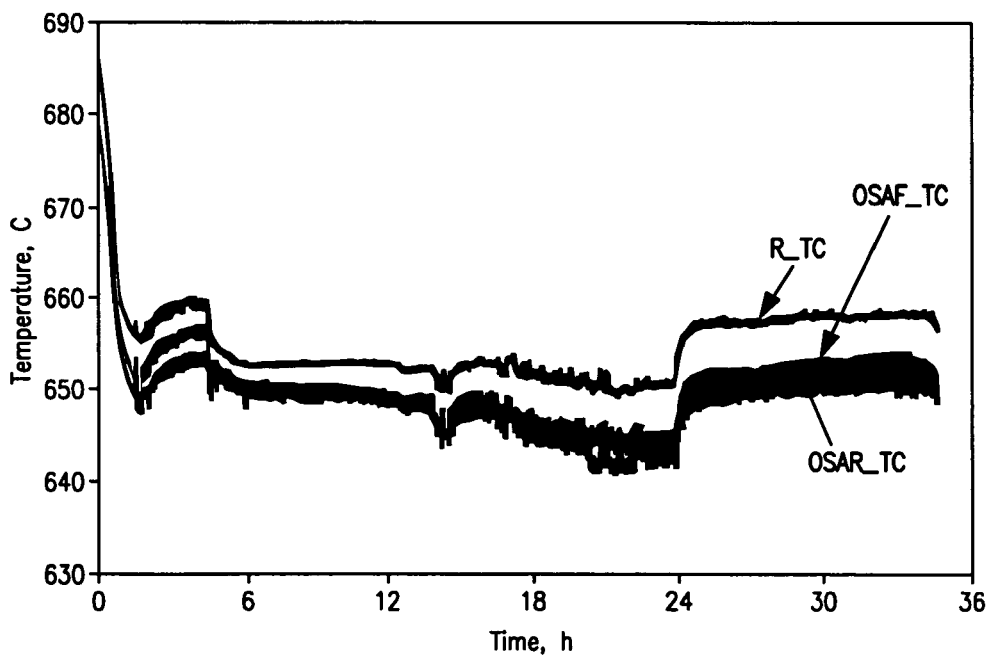
FIG. 8 illustrates the temperature variations measured using the multi-functional sensor system at 3 different cell locations in the electrochemical reduction of a 1 kg-batch $UO_2$ charge in a LiCl-1 wt % $Li_2O$ melt at 650° C. R_TC refers to the R(saturated) location at the cathode while OSAF_TC and OSAR_TC refer to the location of the two R(sensing) electrodes at the two anodes in the cell.

FIG. 8 illustrates the temperature variations measured using the multi-functional sensor system at 3 different cell locations in the electrochemical reduction of a 1 kg-batch $UO_2$ charge in a LiCl-1 wt % $Li_2O$ melt at 650° C. R_TC refers to the R(saturated) location at the cathode while OSAF_TC and OSAR_TC refer to the location of the two R(sensing) electrodes at the two anodes in the cell.

Therefore, the electrodes have been constructed to include thermocouples. The nickel sheathing of the thermocouple serves as the nickel electrode and the voltage lead. The thermocouple wires are insulated from the sheathing. Using the actual measured temperature values, the electrode potential and concentration signal can be corrected for precise values. The multi-functionality of the system makes possible mapping of resistance, concentration, and temperature distributions in production cells. These are important parameters for optimizing cell operations.

Alternate Embodiments

Although the sketches of the sensor system show two separate sensors, the two sensors (saturated and sensing) can be combined into a single piece with the appropriate connections for potential, concentration, and temperature measurements.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. All ranges disclosed herein also encompass any and all possible subranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like refer to ranges which can be subsequently broken down into sub-ranges as discussed above. Accordingly, the invention is limited only by the following claims and equivalents thereto.

All publications and patent documents cited in this application are incorporated by reference in their entirety for all purposes to the same extent as if each individual publication or patent document were so individually denoted.

We claim:

1. A multi-functional electrochemical sensor system comprising:
    a saturated reference electrode;
    a sensing reference electrode;
    the saturated electrode having a first outer tube, the first outer tube having a central aperture running the length of the first outer tube, the central aperture of the first outer tube having an upper and lower end;
    the lower end of the central aperture of the first outer tube being plugged by a high density diffusion barrier;
    a first coaxial thermocouple having a thermosensing end, a data retrieval end, an outer conducting sheath, and an inner thermosensor;
    the first coaxial thermocouple positioned within the first outer tube so that the thermosensing end of the thermocouple extends into the lower end of the central aperture of the first outer tube above the high density diffusion barrier;
    a first inner metal oxide sensing phase and a second inner metal oxide sensing phase the first and second inner metal oxide sensing phases contained in, at least the lower end of the central aperture of the first outer tube above the high density diffusion barrier and coating at least a portion of the thermosensing end of the first thermocouple;
    a first voltage wire connecting the outer conducting sheath of the first coaxial thermocouple to the data acquisition system;
    a set of first data wires connecting the inner thermosensor of the first coaxial thermocouple to the data acquisition system;
    the sensing electrode having a second outer tube, the second outer tube having a central aperture running the length of the second outer tube, the central aperture of the second outer tube having an upper and lower end;
    the lower end of the central aperture of the second outer tube being plugged by a low density, highly porous diffusion barrier;
    a second coaxial thermocouple having a thermosensing end, a data retrieval end, an outer conducting sheath, and an inner thermosensor;
    the second coaxial thermocouple positioned within the second outer tube so that the thermosensing end of the thermocouple extends into the lower end of the central aperture of the second outer tube above the low density diffusion barrier;
    a third inner metal oxide sensing phase, the third inner metal oxide sensing phase coating at least a portion of the thermosensing end of the second thermocouple;
    a second voltage wire connecting the outer conducting sheath of the second coaxial thermocouple to the data acquisition system;
    a set of second data wires connecting the inner thermosensor of the second coaxial thermocouple to the data acquisition system.

2. The multi-functional electrochemical sensor as set out in claim 1, wherein the system is capable of measuring temperature dependent potentials and ion concentrations.

3. The multi-functional electrochemical sensor as set out in claim 1, wherein the first and second outer tubes are constructed of a high density ceramic.

4. The multi-functional electrochemical sensor as set out in claim 1, wherein the first and second outer tubes are constructed from materials selected from the group consisting of MgO, $Al_2O_3$, and combinations thereof.

5. The multi-functional electrochemical sensor as set out in claim 1, wherein the high density diffusion barrier of the saturated reference electrode minimizes leakage of the second metal oxide inner sensing phase from the saturated reference electrode.

6. The multi-functional electrochemical sensor as set out in claim 1, further comprising a means for attaching the first coaxial thermocouple to the first outer tube to keep the first thermocouple in place, and a means for attaching the second coaxial thermocouple to the second outer tube to keep the second thermocouple in place.

7. The multi-functional electrochemical sensor as set out in claim 1, wherein the data transmission end of the first coaxial thermocouple extends out of the upper end of the first outer tube, and wherein the data transmission end of the second coaxial thermocouple extends out of the upper end of the second outer tube.

8. The multi-functional electrochemical sensor as set out in claim 1, wherein the outer conducting sheaths of the first and second coaxial thermocouples are constructed from the group of materials consisting of: Ni, Fe, Li, Ca, and combinations thereof.

9. The multi-functional electrochemical sensor as set out in claim 1, wherein the outer conducting sheaths of the first and second coaxial thermocouples are constructed from Ni.

10. The multi-functional electrochemical sensor as set out in claim 1, wherein the first and third inner metal oxide sensing phases are NiO.

11. The multi-functional electrochemical sensor as set out in claim 1, wherein the first and third inner sensing phase are made up of metal oxides selected from a group consisting of NiO, $Fe_3O_4$, $Fe_2O_3$, and combinations thereof.

12. The multi-functional electrochemical sensor as set out in claim 1, wherein the second inner phase is selected from the group consisting of $Li_2O$, CaO, and combinations thereof.

13. The multi-functional electrochemical sensor as set out in claim 1, wherein the outer conducting sheath of the first and second coaxial thermocouples are Ni, the first and third inner sensing phases are NiO, and the second inner phase of the saturated electrode is $Li_2O$.

14. The multi-functional electrochemical sensor as set out in claim 1, wherein the high density diffusion barrier of the saturated reference electrode is constructed from a group of materials consisting of MgO, $Al_2O_3$, and combinations thereof and the low density diffusion barrier of the sensing reference electrode is constructed from a group of materials consisting of MgO, $Al_2O_3$ and combinations thereof.

15. The multi-functional electrochemical sensor as set out in claim 1, wherein the thermosensors of the first and second thermocouples are positioned near their thermosensing ends.

16. The multi-functional electrochemical sensor as set out in claim 1, wherein the first and second thermocouples are insulated, ungrounded, k-type thermocouples.

17. A multi-functional electrochemical system comprising:
a cathode, an anode, a multifunctional sensor system, and first bulk electrolyte in communication with said cathode, anode and multi-functional sensor system;
wherein the multi-functional sensor system is that of claim 2.

18. The multi-functional electrochemical system as set out in claim 17, wherein the bulk electrolyte is selected from the group consisting of: LiCl, and $CaCl_2$.

19. The multi-functional electrochemical system as set out in claim 17, wherein the bulk electrolyte is selected from the group consisting of: a chloride, fluoride, sulfide, bromide and iodide.

20. The multi-functional electrochemical system as set out in claim 17, wherein the outer conducing sheath of the first and second coaxial thermocouples are Ni and the first and third inner sensing phases are NiO.

* * * * *